(12) United States Patent
Fernandez et al.

(10) Patent No.: US 9,732,028 B2
(45) Date of Patent: Aug. 15, 2017

(54) PROCESS FOR PURIFICATION OF DIPHENYL CARBONATE FOR THE MANUFACTURING OF HIGH QUALITY POLYCARBONATE

(71) Applicant: SABIC GLOBAL TECHNOLOGIES B.V., Bergen op Zoom (NL)

(72) Inventors: Ignacio Vic Fernandez, Santo Angel (ES); Mykhaylo Lyakhovych, Murcia (ES); Sergio Ferrer Nadal, Granada (ES)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 367 days.

(21) Appl. No.: 14/206,692

(22) Filed: Mar. 12, 2014

(65) Prior Publication Data

US 2014/0275473 A1  Sep. 18, 2014

(30) Foreign Application Priority Data

Mar. 15, 2013  (EP) ..................... 13382087

(51) Int. Cl.
*B01D 11/00*   (2006.01)
*C02F 1/26*    (2006.01)
(Continued)

(52) U.S. Cl.
CPC ............... *C07C 68/08* (2013.01); *C02F 1/02* (2013.01); *C02F 1/04* (2013.01); *C02F 1/52* (2013.01); *C02F 1/62* (2013.01); *C02F 1/64* (2013.01); *C07C 68/02* (2013.01); *C07C 68/04* (2013.01); *C07C 68/06* (2013.01); *C07C 69/96* (2013.01); *C08G 64/04* (2013.01); (Continued)

(58) Field of Classification Search
None
See application file for complete search history.

(56) References Cited

U.S. PATENT DOCUMENTS 4,508,890 A * 4/1985 Schmidt ............... C08G 64/00
                                                    528/167
5,344,954 A * 9/1994 Schon .................. C07C 68/06
                                                    203/38
(Continued)

FOREIGN PATENT DOCUMENTS

EP   0633241 A1   1/1995
EP   2778186 A1   9/2014
GB    883619     12/1961

OTHER PUBLICATIONS

U.S. Appl. No. 14/207,806, filed Mar. 13, 2014.
(Continued)

*Primary Examiner* — Clare Perrin
(74) *Attorney, Agent, or Firm* — Cantor Colburn LLP

(57) ABSTRACT

A process for purifying a diaryl carbonate, comprises introducing an aqueous stream to a diaryl carbonate stream that comprises a metal contaminant, wherein the aqueous stream reacts with the metal contaminant to form a precipitate; wherein introducing the aqueous stream to the diaryl carbonate stream results in introducing 100 to 10,000 ppm water based on the total composition of the diaryl carbonate stream and the aqueous stream; removing the precipitate via one or both of a separation column and a filter to result in a purified diaryl carbonate.

13 Claims, 3 Drawing Sheets

(51) Int. Cl.

| | |
|---|---|
| *C07C 69/96* | (2006.01) |
| *C02F 1/52* | (2006.01) |
| *B01D 21/01* | (2006.01) |
| *B03D 3/00* | (2006.01) |
| *C07C 68/08* | (2006.01) |
| *C07C 68/02* | (2006.01) |
| *C07C 68/04* | (2006.01) |
| *C07C 68/06* | (2006.01) |
| *C08G 64/04* | (2006.01) |
| *C02F 1/62* | (2006.01) |
| *C02F 1/64* | (2006.01) |
| *C02F 1/02* | (2006.01) |
| *C02F 1/04* | (2006.01) |
| *B01D 11/04* | (2006.01) |
| *C02F 1/00* | (2006.01) |
| *C02F 1/68* | (2006.01) |
| *B01D 21/00* | (2006.01) |
| *B01D 37/00* | (2006.01) |
| *C02F 101/22* | (2006.01) |
| *C02F 101/20* | (2006.01) |
| *C02F 103/36* | (2006.01) |

(52) U.S. Cl.
CPC .... *C02F 2101/20* (2013.01); *C02F 2101/203* (2013.01); *C02F 2101/206* (2013.01); *C02F 2101/22* (2013.01); *C02F 2103/36* (2013.01)

(56) References Cited

U.S. PATENT DOCUMENTS

| | | | |
|---|---|---|---|
| 5,349,043 | A | 9/1994 | Kuze et al. |
| 5,498,319 | A * | 3/1996 | Ehlinger ................. C07C 68/08 203/39 |
| 6,090,737 | A * | 7/2000 | Ofori .................... C07C 68/005 210/758 |
| 6,410,678 | B1 | 6/2002 | Ishida et al. |
| 6,455,667 | B1 | 9/2002 | Kimura et al. |
| 6,512,148 | B1 | 1/2003 | Yamamoto et al. |
| 6,669,850 | B1 | 12/2003 | Fuller et al. |
| 7,812,189 | B2 | 10/2010 | Fukuoka et al. |
| 2005/0014965 | A1* | 1/2005 | Dahlmann ............ C07C 68/005 558/270 |
| 2011/0034588 | A1 | 2/2011 | Boucher et al. |

OTHER PUBLICATIONS

European Search Report for European Application No. 13382087.8; European Filing Date Aug. 14, 2013; Date of Mailing Nov. 18, 2013; 7 pages.

International Search Report for International Application No. PCT/IB2014/059698; International Filing Date Mar. 12, 2014; Date of Mailing Jan. 7, 2015; 6 pages.

Written Opinion for International Application No. PCT/IB2014/059698; International Filing Date Mar. 12, 2014; Date of Mailing Jan. 7, 2015; 7 pages.

\* cited by examiner

PROCESS FOR PURIFICATION OF DIPHENYL CARBONATE FOR THE MANUFACTURING OF HIGH QUALITY POLYCARBONATE

CROSS-REFERENCE TO RELATED APPLICATION

This application claims the benefit of European Patent Application Serial No. 13382087.8 filed Mar. 15, 2013. The related application is incorporated herein by reference.

BACKGROUND

The preparation of polycarbonate can be achieved through the melt reaction of an aromatic dihydroxy compound and a diaryl carbonate. There are several methods by which diaryl carbonate can be produced including decarbonylating a diaryl oxalate in the presence of a catalyst while removing a carbon monoxide by product; reacting an aromatic hydroxy compound with phosgene in the gas phase in the presence of a heterogeneous catalyst, for example, the direct phosgenation of phenol; reacting an aromatic hydroxy compound, carbon monoxide, and oxygen in the presence of a redox catalyst and an organic salt; or reacting an aromatic hydroxy compound with a dialkyl carbonate. A specific example of a non-phosgene route to synthesize the diaryl carbonate of diphenyl carbonate (DPC) can be achieved with the use of respective catalysts through the transesterification of dimethyl carbonate (DMC) and phenol to produce phenyl methyl carbonate (PMC) as shown in Reaction (1),

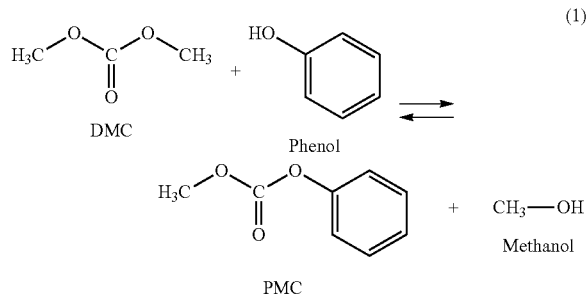

followed by the subsequent disproportionation of PMC to produce diphenyl carbonate (DPC) as shown in Reaction (2),

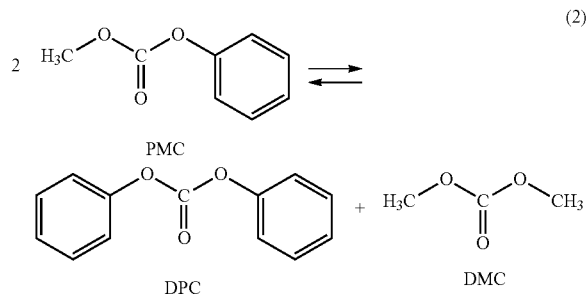

with an additional formation of small amounts of an alkyl aryl ether (anisole) as the main reaction byproduct.

The formation of diaryl carbonates in any of the aforementioned reaction schemes or in any other reaction scheme can generally be facilitated through the use of a catalyst. Unfortunately, any residual metal from said catalyst can result in discoloration of the resultant polycarbonate and a reduction in the color stability of the polycarbonate. Furthermore, the metal from the catalyst used in the formation of the diaryl carbonate can cause corrosion of the process vessels that can result in a further source of metal corrosion, in addition to any degradation of the process vessels that can occur independently of the catalyst.

Current processes to purify diphenyl carbonate from the catalyst involve the use of a set of separating columns, in which the transesterification reaction mixture is introduced to a high boiling point material separating column where a purified diphenyl carbonate is produced as a top component and diphenyl carbonate containing the catalyst exits as a bottom component. However, an amount of residual catalyst is generally still present after said purification, due to their relative volatility or entrainment. This remaining amount of catalyst can result in discoloration when used as a reactant in the polymerization of polycarbonate.

An improved method to purify the diaryl carbonate reactant from metal contaminants that arise from either or both of the catalyst or the degradation of the process vessels would therefore be desirable in the production of polycarbonate for use in good color stability and high transparency applications.

BRIEF SUMMARY

Disclosed herein are methods of making a purified diaryl carbonate and the diaryl carbonate produced therefrom.

In an embodiment, a process for purifying a diaryl carbonate, comprises introducing an aqueous stream to a diaryl carbonate stream that comprises a metal contaminant, wherein the aqueous stream reacts with the metal contaminant to form a precipitate; wherein introducing the aqueous stream to the diaryl carbonate stream results in introducing 100 to 10,000 ppm water based on the total weight of the diaryl carbonate stream and the aqueous stream; removing the precipitate via one or both of a separation column and a filter to result in a purified diaryl carbonate; wherein when the removing utilizes the separation column, the process further comprises: removing a bottom stream comprising the precipitate from the separation column; removing a top stream from the separation column; directing a top stream first portion into the separation column and collecting a top stream second portion, wherein the top stream second component comprises the purified diaryl carbonate.

In another embodiment, a process for purifying a diaryl carbonate can comprise: introducing an aqueous stream to a diaryl carbonate stream that comprises molten diaryl carbonate and a metal contaminant, wherein the aqueous stream reacts with the metal contaminant to form a precipitate; wherein introducing the aqueous stream to the diaryl carbonate stream results in introducing 100 to 10,000 ppm water based on the total composition of the diaryl carbonate stream and the aqueous stream; and removing the precipitate via one or both of a separation column and a filter to result in a purified diaryl carbonate.

These and other features and characteristics are more particularly described below in view of the figures and detailed description.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
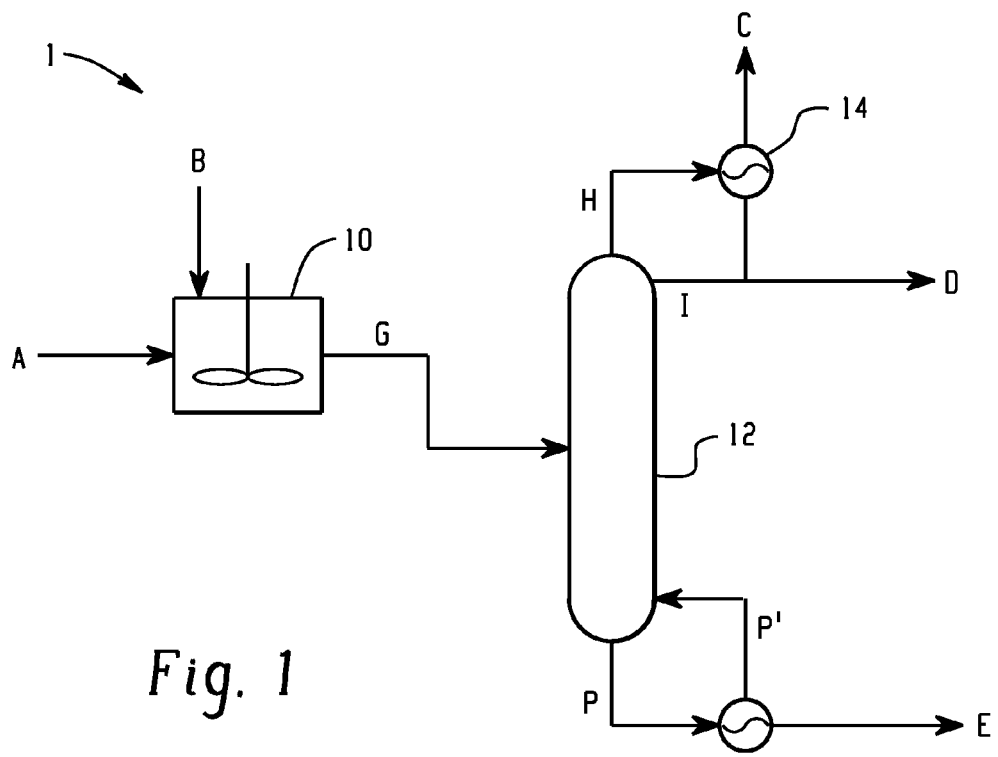
FIG. 1 is a schematic representation of an example of a diaryl carbonate purification scheme by introducing an aqueous media to a diaryl carbonate.

Synthetic routes to produce diaryl carbonate can result in metal contaminated diaryl carbonate compositions. The metal contaminant can arise from one or both of the use of a catalyst to facilitate the formation of the diaryl carbonate and the corrosion of process equipment. The metal contaminants can be in organometallic or inorganic forms. The Applicants surprisingly found that introducing an aqueous stream to the diaryl carbonate stream, resulted in the conversion of the metal contaminant(s) into their inorganic form, most likely into oxide and/or hydroxide forms, such that it could easily be separated as a solid precipitate by distillation and/or filtration. The Applicants surprisingly found that the aqueous stream could be introduced without remarkably decreasing the amount of resultant diaryl carbonate that could be purified. This second surprising feature was especially surprising as it is known that water can react with diaryl carbonates such as that of diphenyl carbonate.

The metal contaminant can comprise titanium, lead, tin, zirconium, molybdenum, niobium, vanadium, iron, zinc, aluminum, yttrium, lanthanum, hafnium, tungsten, neodymium, samarium, ytterbium, copper, chromium, nickel, manganese, bismuth, niobium, or a combination comprising one or more of the foregoing. The Applicants found that the purification process can result in the removal of greater than or equal to 80 wt %, specifically, greater than or equal to 90 wt % of the metal contaminant based on the total weight of the metal contaminant present in the diaryl carbonate stream. The purified diaryl carbonate can comprise less than or equal to 38 parts per billion by weight (ppb), specifically, less than or equal to 23 ppb of molybdenum; less than or equal to 38 ppb, specifically, less than or equal to 23 ppb vanadium; less than or equal to 38 ppb, specifically, less than or equal to 23 ppb chromium; less than or equal to 85 ppb, specifically, less than or equal to 57 ppb titanium; less than or equal to 425 ppb, specifically, less than or equal to 284 ppb of niobium; less than or equal to 38 ppb, specifically, less than or equal to 23 ppb of nickel; less than or equal to 12 ppb, specifically, less than or equal to 6 ppb zirconium; less than or equal to 12 ppb, specifically, less than or equal to 6 ppb of iron, or a combination comprising one or more of the foregoing. A polycarbonate polymerized from the purified diaryl carbonate can comprise less than or equal to 33 parts per billion by weight (ppb), specifically, less than or equal to 20 ppb of molybdenum; less than or equal to 33 ppb, specifically, less than or equal to 20 ppb vanadium; less than or equal to 33 ppb, specifically, less than or equal to 20 ppb chromium; less than or equal to 75 ppb, specifically, less than or equal to 50 ppb titanium; less than or equal to 375 ppb, specifically, less than or equal to 250 ppb of niobium; less than or equal to 33 ppb, specifically, less than or equal to 20 ppb of nickel; less than or equal to 10 ppb, specifically, less than or equal to 5 ppb zirconium; less than or equal to 10 ppb, specifically, less than or equal to 5 ppb of iron, or a combination comprising one or more of the foregoing. The Applicants also found that the purification process can result in a high yield of the purified diaryl carbonate of greater than or equal to 90%, specifically, greater than or equal to 95%.

Polycarbonates polymerized from such a purified diaryl carbonate can be used for transparent applications due to one or more of their low color of, for example a Comission Internationale de l'Eclairage (CIE) b* index of less than or equal to 0.5, specifically, less than or equal to 0.15 as determined by spectrophotometry, and high light transmission of, for example, greater than or equal to 89% as determined by spectrophotometry.

Polycarbonates polymerized from such a purified diaryl carbonate can have a yellowness index of, for example less, than or equal to 3, specifically, less than or equal to 2.5 as determined by ASTM D1925, after 2 hours of aging at 250° C.

The diaryl carbonate that can be purified can have the formula (I)

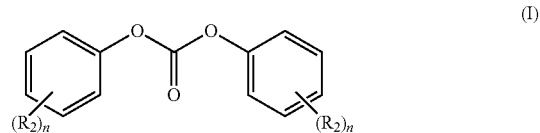

(I)

wherein n is an integer 1 to 3 and each $R_2$ is independently linear or branched; optionally substituted; $C_{1-34}$ alkyl, specifically, $C_{1-6}$ alkyl, more specifically, $C_{1-4}$ alkyl; $C_{1-34}$ alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl.

The diaryl carbonate of the general formula (I) can comprise diphenyl carbonate, methylphenyl-phenyl carbonates and di-(methylphenyl)carbonates (wherein the methyl group can be in any desired position on the phenyl rings), dimethylphenyl-phenyl carbonates and di-(dimethylphenyl) carbonates (wherein the methyl groups can be in any desired position on the phenyl rings, for example 2,4-, 2,6-, 3,5- or 3,4-dimethylphenyl), chlorophenyl-phenyl carbonates and di-(chlorophenyl)carbonates (wherein the chloro atom can be in any desired position on the phenyl rings, for example 2-, 3-, or 4-chlorophenyl), 4-ethylphenyl-phenyl carbonate, di-(4-ethylphenyl)carbonate, 4-n-propylphenyl-phenyl carbonate, di-(4-n-propylphenyl)carbonate, 4-isopropylphenyl-phenyl carbonate, di-(4-isopropylphenyl)carbonate, 4-n-butylphenyl-phenyl carbonate, di-(4-n-butylphenyl)carbonate, 4-isobutylphenyl-phenyl carbonate, di-(4-isobutylphenyl) carbonate, 4-tert-butylphenyl-phenyl carbonate, di-(4-tert-butylphenyl)carbonate, 4-n-pentylphenyl-phenyl carbonate, di-(4-npentylphenyl)carbonate, 4-n-hexylphenyl-phenyl carbonate, di-(4-n-hexylphenyl)carbonate, 4-isooctylphenyl-phenyl carbonate, di-(4-isooctylphenyl)carbonate, 4-n-nonylphenyl-phenyl carbonate, di-(4-n-nonyl-phenyl)carbonate, 4-cyclohexylphenyl-phenyl carbonate, di-(4-cyclohexylphenyl)carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl)carbonate, (1-naphthyl)-phenyl carbonate, (2-naphthyl)-phenyl carbonate, di-(1-naphthyl)carbonate, di-(2-naphthyl)carbonate, 4-(1-naphthyl)-phenyl-phenyl carbonate, 4-(2-naphthyl)-phenyl-phenyl carbonate, di-[4-(1-naphthyl)-phenyl]carbonate, di-[4-(2-naphthyl)phenyl]carbonate, 4-phenoxyphenyl-phenyl carbonate, di-(4-phenoxyphenyl)carbonate, 3-pentadecylphenyl-phenyl carbonate, di-(3-pentadecylphenyl) carbonate, 4-tritylphenyl-phenyl carbonate, di-(4-tritylphenyl)carbonate, methyl salicylate-phenyl carbonate, di-(methyl salicylate) carbonate, ethyl salicylate-phenyl carbonate, di-(ethyl salicylate) carbonate, n-propyl salicylate-phenyl carbonate, di-(n-propyl salicylate) carbonate, isopropyl salicylate-phenyl carbonate, di-(isopropyl salicylate) carbonate, n-butyl salicylate-phenyl carbonate, di-(n-butyl salicylate) carbonate, isobutyl salicylate-phenyl carbonate, di-(isobutyl salicylate) carbonate, tert-butyl salicylate-phenyl carbonate, di-(tert-butyl salicylate) carbonate, di-(phenyl salicylate)-carbonate, di-(benzyl salicylate) carbonate, and combinations comprising one or more of the foregoing. The diaryl carbonate can comprise diphenyl carbonate.

There are several methods by which diaryl carbonate can be produced. One method for producing diaryl carbonate includes decarbonylating a diaryl oxalate (such as diphenyl oxalate) in the presence of a decarbonylation catalyst while removing a carbon monoxide by product. The decarbonylation reaction can occur in the liquid phase. The diaryl oxalate can comprise a diaryl oxalate of the formula: ArO(C=O)—(C=O)OAr, where each Ar independently can be an aromatic hydrocarbon group having 6 to 14 carbon atoms, for example, Ar can be a phenyl group, which can be substituted with at least one selected from alkyl groups having 1 to 6 carbon atoms (such as methyl, ethyl, propyl, butyl, pentyl, and hexyl), alkoxy groups having 1 to 6 carbon atoms (such as methoxy, propoxy, butoxy, pentoxy, and hexoxy), and halogen atoms (such as fluorine, chlorine, bromine, and iodine). The diaryl oxalate can comprise diphenyl oxalate, m-cresyl oxalate, m-cresyl phenyl oxalate, p-cresyl oxalate, p-cresyl phenyl oxalate, dinaphthyl oxalate, bis(diphenyl)oxalate, bis(chlorophenyl)oxalate, or a combination comprising of one or more of the forgoing. The diaryl oxalate can contain less than or equal to 5 parts per million by weight (ppm), specifically, less than or equal to 2 ppm of a hydrolysable halogen.

The diaryl oxalate can be prepared by transesterifying a dialkyl oxalate (such as dimethyl oxalate) with a hydroxyaryl compound (such as phenol) in the presence of a transesterification catalyst, where the transesterification reaction can occur in the liquid phase. The dialkyl oxalate can comprise one or more lower dialkyl oxalates of which the alkyl group comprises 1 to 6 carbon atoms, for example dimethyl oxalate, diethyl oxalate, dipropyl oxalate, dibutyl oxalate, dipentyl oxalate, and dihexyl oxalate.

The transesterification catalyst useful for the preparation of the diaryl oxalate from the dialkyl oxalate and the hydroxyaryl compound can comprise at least one of, for example, compounds and complexes of alkali metals, compounds and complexes of cadmium and zirconium, lead-containing compounds, iron-containing compounds, copper group metal compounds, silver-containing compounds, zinc-containing compounds, organic tin compounds, and Lewis acid compounds of aluminum, titanium, and vanadium. The decarbonylation catalyst can comprise at least one organic phosphorus compound (such as an organic phosphine compound, an organic phosphine oxide compound, an organic phosphine dihalide compound, and an organic phosphonium salt compound). The decarbonylation catalyst can contain a halogen, for example, on the phosphorus containing compound or as a separate halogen compound. Another method for producing diaryl carbonate includes reacting an aromatic hydroxy compound and carbon monoxide in the presence of oxygen, where the reaction can be facilitated by a catalyst and an optional organic salt. For example, the reaction can be the oxidative carbonylation of phenol, where the reaction can occur in a fixed-bed reactor or in an autoclave reactor. Suitable catalysts for the oxidative carbonylation of aromatic hydroxy compounds include a palladium catalyst. The palladium catalyst can be in solvated form (such as $PdBr_2$ promoted with transition metal oxides and solvated promoters, including one or more of $N(Bu)_4Br$, $Mn(AcAc)_2$, $NaO(C_6H_5)$ and the like), suspended form with Pd supported on pulverized $TiO_2$, or extrudate form with Pd supported on rare earth metal oxide. The palladium catalyst can comprise $Pd(OAc)_2$/hydrotalcite. As used herein Bu means butyl, AcAc means acetylacetonate, and OAc means acetate. The catalyst can comprise a cocatalyst, such as a cesium compound, a manganese compound, a cobalt compound, a copper compound, hydroquinone, benzoquinone, naphthoquinone, or a combination comprising one or more of the foregoing. The organic salt can comprise, for example, $^nBu_4NBr$, $^nBu_4PBr$, PPNBr, and the like.

The aromatic hydroxy compound can comprise an aromatic hydroxy compound of the formula (III)

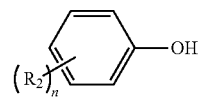

(III)

wherein n and $R_2$ are defined as above in formula (I).

The aromatic hydroxy compound can comprise phenol, o-, m- or p-cresol, dimethylphenol (wherein the methyl groups can be in any desired position on the phenol ring, for example 2,4-, 2,6- or 3,4-dimethylphenol), o-, m- or p-chlorophenol, o-, m- or p-ethylphenol, o-, m- or p-n-propylphenol), 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)-phenol, biphenyl-4-ol, 1-naphthol, 2-naphthol, 4-(1-naphthyl)phenol, 4-(2-naphthyl)phenol, 4-phenoxyphenol, 3-pentadecylphenol, 4-tritylphenol, salicylic acid methyl ester, salicylic acid ethyl ester, salicylic acid n-propyl ester, salicylic acid isopropyl ester, salicylic acid n-butyl ester, salicylic acid isobutyl ester, salicylic acid tert-butyl ester, salicylic acid phenyl ester, salicylic acid benzyl ester, or a combination comprising one or more of the foregoing.

The aromatic hydroxy compound can comprise phenol, 4-tert-butylphenol, biphenyl-4-ol, 4-(1-methyl-1-phenylethyl)-phenol, or a combination comprising one or more of the foregoing.

Other methods for producing diaryl carbonate include reacting an aromatic hydroxy compound, which can comprise the aromatic hydroxy compound of formula III, with phosgene in either the gas or liquid phase, for example, the direct phosgenation of phenol and reacting an aromatic hydroxy compound with a dialkyl carbonate, where said reactions can occur in the presence of a transesterification catalyst. The aromatic hydroxy compound and either phosgene or the dialkyl carbonate can be added in a molar ratio of 1:0.1 to 1:10, specifically, 1:0.2 to 1:5, more specifically, 1:0.5 to 1:3. The indicated molar ratio does not take into account any recycled components that can be added back to the production column.

The dialkyl carbonate can comprise the dialkyl carbonate of the formula (II)

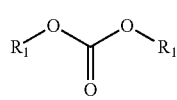

(II)

wherein each $R_1$ independently is linear or branched; optionally substituted; $C_{1-34}$ alkyl, specifically, $C_{1-6}$ alkyl, more specifically, $C_{1-4}$ alkyl. The $C_{1-4}$ alkyl can comprise methyl, ethyl, n-propyl, isopropyl, n-butyl, sec-butyl, tert-butyl, or a combination comprising of one or more of the foregoing. The $C_{1-6}$ alkyl can comprise n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, or a combination comprising of one or more of the foregoing. The $C_1$-$C_{34}$-alkyl can comprise n-heptyl, n-octyl, pinacyl, adamantyl, an isomeric menthyl, n-nonyl, n-decyl, n-dodecyl, n-tridecyl, n-tetradecyl, n-hexadecyl, or n-octadecyl, or a combination comprising of one or more of the foregoing.

The dialkyl carbonates can comprise dimethyl carbonate, diethyl carbonate, dipropyl carbonate (e.g., di(n-propyl) carbonate, and/or di(isopropyl)carbonate), dibutyl carbonate (e.g., di(n-butyl)carbonate, di(sec-butyl)carbonate, and/or di(tert-butyl) carbonate), dihexyl carbonate, or a combination comprising one or more of the foregoing.

A catalyst can be used to facilitate the reaction between the aromatic hydroxy compound and either phosgene or the dialkyl carbonate. The catalyst can be a homogeneous catalyst and/or a heterogeneous catalyst, wherein a heterogeneous catalyst comprises two or more catalysts. The catalyst can comprise hydrides, oxides, hydroxides, alcoholates, amides and other salts of alkali and alkaline earth metals, such as of lithium, sodium, potassium, rubidium, cesium, magnesium and calcium, specifically, lithium, sodium, potassium, magnesium, calcium, or a combination comprising one or more of the foregoing. Salts of the alkali and alkaline earth metals can also be salts of organic or inorganic acids, such as of acetic acid, propionic acid, butyric acid, benzoic acid, stearic acid, carbonic acid (carbonates or hydrogen carbonates), phosphoric acid, hydrocyanic acid, thiocyanic acid, boric acid, cinnamic acid, $C_{14}$-stannonic acids, antimonic acid, or a combination comprising one or more of the foregoing. Suitable compounds of the alkali and alkaline earth metals can be the oxides, hydroxides, alcoholates, acetates, propionates, benzoates, carbonates, and hydrogen carbonates. The mentioned alkali or alkaline earth metal compounds can be used in amounts of 0.001 to 2 weight percent (wt %), specifically, 0.005 to 0.9 wt %, and more specifically, 0.01 to 0.5 wt %, based on the weight of the reaction mixture to be reacted.

Further catalysts which can be used can comprise a metal such as titanium, lead, tin, zirconium, molybdenum, niobium, vanadium, uranium, iron, zinc, aluminum, yttrium, lanthanum, hafnium, tungsten, neodymium, samarium, ytterbium, copper, or a combination comprising one or more of the foregoing. Such metals can be used in metal catalyst compounds such as $AlX_3$, $TiX_3$, $UX_4$, $TiX_4$, $VOX_3$, $VX_5$, $ZnX_2$, $FeX_3$, $PbX_2$ and $SnX_4$, wherein X represents halogen, acetoxy, alkoxy, aryloxy radicals, or a combination comprising one or more of the foregoing. The metal compound of $AlX_3$, $TiX_4$, $PbX_2$, and $SnX_4$ can comprise titanium tetrachloride, titanium tetramethoxide, titanium tetraphenoxide, titanium tetraethoxide, titanium tetraisopropylate, titanium tetradodecylate, tin tetraisooctylate and aluminium triisopropylate. The mentioned metal compounds can be used in an amount of 0.001 to 10 wt %, more specifically, 0.005 to 5 wt %, and even more specifically, 0.01 to 7 wt %, based on the weight of the reaction mixture to be reacted.

Further catalysts which can be used can be organotin compounds of the general formula $(R^{11})_{4-x}$—$Sn(Y)_x$, wherein Y represents a radical $OCOR^{12}$, OH, or OR, wherein $R^{12}$ represents $C_{1-12}$ alkyl, $C_{6-12}$ aryl or $C_{7-13}$ alkylaryl, $R^{11}$ independently of $R^{12}$ has the meaning of $R^{12}$ and x represents an integer 1 to 3; dialkyltin compounds having from 1 to 12 carbon atoms in the alkyl radical; or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid, octylstannonic acid, or a combination comprising one or more of the foregoing. The organotin compound can be used in an amount of 0.001 to 20 wt %. The organotin compound can comprise polymeric tin compounds of the formula —[—$RR^{11}Sn$—O—]—, in which R and $R^{11}$ independently of one another have the meaning given above for $R^{12}$, for example poly[oxy(dibutylstannylene)], poly[oxy(dioctyl stannylene)], poly [oxy (butylphenyl stannylene)], and poly[oxy(diphenylstannylene)], polymeric hydroxystannoxanes of the formula —[—RSn(OH)—O—]—, for example poly(ethylhydroxystannoxane), poly(butylhydroxystannoxane), poly(octylhydroxysnoxane), poly(undecylhydroxystannoxane), and poly(dodecylhydroxystannoxanes), or a combination comprising one or more of the foregoing. The polymeric tin compounds can be used in an amount of 0.001 to 20 wt %, specifically, 0.005 to 5 wt %, based on dialkyl carbonate. Further tin compounds, which can be used are Sn(II) oxides of the general formula X—$R^{13}Sn$—O—$R^{13}Sn$—Y, wherein X and Y independently of one another represent OH, SCN, $OR^{14}$, $OCOR^{14}$ or halogen and $R^{13}$ represents alkyl, aryl, wherein $R^{14}$ has the meaning given above for $R^{12}$.

Further catalysts are lead compounds, optionally together with triorgano-phosphanes, a chelate compound or an alkali metal halide, for example lead diphenoxide, $Pb(OH)_2$-$2PbCO_3$, $Pb(OCO$—$CH_3)_2$, $Pb(OCO$—$CH_3)_2.2LiCl$, $Pb(OCO$—$CH_3)_3.2PPh_3$, as well as other lead(II) and lead (IV) compounds, such as PbO, $PbO_2$, red lead, plumbites and plumbates, or a combination comprising one or more of the foregoing. The lead compounds can be present in an amount of 0.001 to 1, specifically, 0.005 to 0.25 mole per mole of dialkyl carbonate.

Further catalysts are iron(III) acetate, also copper salts and/or metal complexes, for example of alkali, zinc, titanium, iron, and combinations comprising one or more of the foregoing. These catalysts can be present in an amount of 0.001 to 1, specifically, 0.005 to 0.25 mole per mole of dialkyl carbonate.

It is further possible to use heterogeneous catalyst systems. Such systems are, for example, mixed oxides of silicon and titanium which are obtainable by common hydrolysis of silicon and titanium halides or titanium dioxides having a high Brunaer, Emmet and Taller (BET) surface area of greater than or equal to 20 meters squared per gram ($m^2/g$).

The catalyst, when homogeneous, can be introduced to the reaction mixture in dissolved or suspended form together with the stream containing the aromatic hydroxy compound. Alternatively, the catalyst can be introduced, for example in the reaction alcohol or a suitable inert solvent. A heterogeneous catalyst can be used in a packed bed, a column, or in special catalytic distillation arrangements, as well as in other arrangements.

As mentioned above, metal from the catalyst used in the production of the diaryl carbonate can cause corrosion of any metal machinery the process mixture comes in contact with, such as one or more of the reaction vessels, distillation columns, heat exchangers, pumps, compressors, storage tanks, instrumentation, transport pipes, and mixing blades. The metal machinery can comprise a metal, where the metal can comprise steel. The corrosion of the process vessel can result in the release of a metal, such as iron, chromium, nickel, molybdenum, copper, titanium, zinc, aluminum, vanadium, niobium, zirconium, manganese, or a combination comprising one or more of the foregoing.

The present purification scheme involves introducing an aqueous stream to a diaryl carbonate stream that comprises a metal contaminant such that the metal contaminant can be precipitated to its oxide and/or hydroxide form. The diaryl carbonate stream can comprise greater than or equal to 50 wt % diaryl carbonate, specifically, greater than or equal to 70 wt % diaryl carbonate, more specifically, greater than or equal to 90 wt % diaryl carbonate, even more specifically, greater than or equal to 95 wt % diaryl carbonate, still more specifically, greater than or equal to 99 wt % diaryl carbonate based on the total weight of the diaryl carbonate stream. The diaryl carbonate stream can comprise molten diaryl carbonate. The diaryl carbonate stream can consist of the molten diaryl carbonate and the metal contaminant.

The aqueous stream can be introduced such that greater than or equal to 100 ppm, specifically, 100 to 10,000 ppm, more specifically, 200 to 8,000 ppm, yet more specifically, 500 to 7,000 ppm, e.g., 1,000 to 7000 ppm, of water is introduced based on the total weight of the diaryl carbonate stream and the aqueous stream. The aqueous stream can comprise sodium bicarbonate (or other salts of the alkali and alkaline earth metals such as carbonates or hydrogen carbonates, phosphates, hydrogen phosphates, borates, acetates, propionates) in addition to water.

The introduction of the aqueous stream can occur at a temperature of greater than or equal to the melting point of the diaryl carbonate in order to ensure that the diaryl carbonate is a molten diaryl carbonate. Further increasing the temperature to a temperature greater than then melting point of the diaryl carbonate, for example, to a temperature of greater than 100° C., can reduce the viscosity of the molten diaryl carbonate. The introduction of the aqueous stream can occur at a temperature of greater than or equal to 80° C., specifically, greater than or equal to 90° C., more specifically, greater than 100° C., even more specifically, 110° C. to 250° C., still more specifically, 120° C. to 250° C.

The introduction of the aqueous stream can occur in the presence 0 to 50 wt %, specifically, 0 to 25 wt %, more specifically, 0 to 1 wt %, even more specifically, 0 wt % of a solvent based on the total weight of the diaryl carbonate stream and the aqueous stream. For example, the diaryl carbonate stream can be free of any added solvent (e.g., no solvent is added to the diaryl carbonate stream prior to the introduction of the aqueous stream). Examples of solvents include aliphatic hydrocarbons (such as pentane, petroleum ether, cyclohexane, and isooctane), aromatic hydrocarbons (such as benzene, toluene, and xylene), chloroaromatic compounds (such as chlorobenzene and dichlorobenzene), ethers (such as dioxane, tetrahydrofuran, tert-butyl methyl ether, and anisole), amides (such as dimethylacetamide and N-methyl-pyrrolidinone), and alcohols (such as tert-butanol, cumyl alcohol, isoamyl alcohol, diethylene glycol, and tetramethylurea).

The introduction of the aqueous stream can be facilitated by the use of a mixing device, where the mixing device can refer to any type of apparatus that is capable of facilitating the necessary contact between the diaryl carbonate stream and water in order to achieve the hydrolysis reaction of the metal contaminant. The mixing device can comprise any type of stirring device and/or static mixer with appropriate mixing elements, and/or a tube with turbulent flow that facilitates the mixing. The mixing device can be a continuously stirred-tank reactor or CSTR.

Once the metal contaminant is precipitated, it can then be easily separated by a separation process utilizing one or both of a separation column and a filter to result in a purified diaryl carbonate. When both a separation column and a filter are used the filter can be upstream of the separation column and/or down stream of separation column. If multiple separation columns are present, a filter can be present upstream and/or downstream of one or more of the separation columns.

When the separation process utilizes a separation column, the separation column can be a distillation column, a reactive distillation column, a catalytic distillation column, or the like. The column can contain concentrating part(s) in the upper portion of the separation column and zone(s) beneath the concentrating part, which can have at least two sections, wherein concentrating part(s) of the separation column can be equipped with intermediate condenser(s). Each of the sections, independently of the others, can have 5 or greater, specifically, 10 or greater theoretical equilibrium stages. At the top of the separation column, the reflux stream can be condensed in a condenser, wherein at least a portion of the condensed vapor can re-enter the separation column. At the bottom of the separation column, the bottom stream can be heated in a reboiler, wherein at least a portion of the heated bottom stream can re-enter the separation column. The aqueous stream can be introduced to the diaryl carbonate stream in a mixing device that is located upstream of the separation column and/or that is located downstream of the condenser and upstream of the separation column. When a mixing device is located downstream of the condenser and upstream of the separation column, the aqueous stream and the diaryl carbonate stream, that is the portion of the reflux stream (also referred to as a top stream first portion) to be reintroduced, are introduced to the mixing device, mixed, and introduced to the separation column. The separation column can comprise a set of cascading separation columns to obtain even higher purity DPC.

When the separation process utilizes a filter, the mesh size of the filter can be less than or equal to 20 micrometers, specifically, less than or equal to 1 micrometer, more specifically, less than or equal to 0.2 micrometers.

The residual water in the purified diaryl carbonate can be less than or equal to 1000 ppm, specifically, less than or equal to 500 ppm, more specifically, less than or equal to 100 ppm.

FIG. 1 illustrates diaryl carbonate purification scheme 1. In purification scheme 1, an aqueous stream B is introduced to diphenyl carbonate A that comprises a metal contaminant in a mixing device 10 such that the metal contaminant(s) react with water in the aqueous stream to precipitate metal, presumably metal oxide(s) and/or metal hydroxide(s). After passing through the mixing device, the diaryl carbonate and the precipitated metals are introduced to a separation column 12 through stream G. The vapor stream H, that exits the top of the separation column, also referred to as the top stream, is condensed in a condenser where the excess of water is removed and then split into a top stream first portion I and a top stream second portion D. The top stream first portion I is reintroduced into the separation column 12 as reflux and the top stream second portion D that comprises the purified diaryl carbonate is collected as product distillate. Water C is removed from the top stream before the top stream is split. The bottom stream P that comprises the precipitate exits the bottom of the separation column can be split into at least a bottom stream first portion P' and a bottom stream second portion E. The bottom stream first portion P' is reintroduced into the separation column 12 and the bottom stream second portion E that comprises diaryl carbonate and precipitated metal contaminant is removed from the system.

Figure 2:
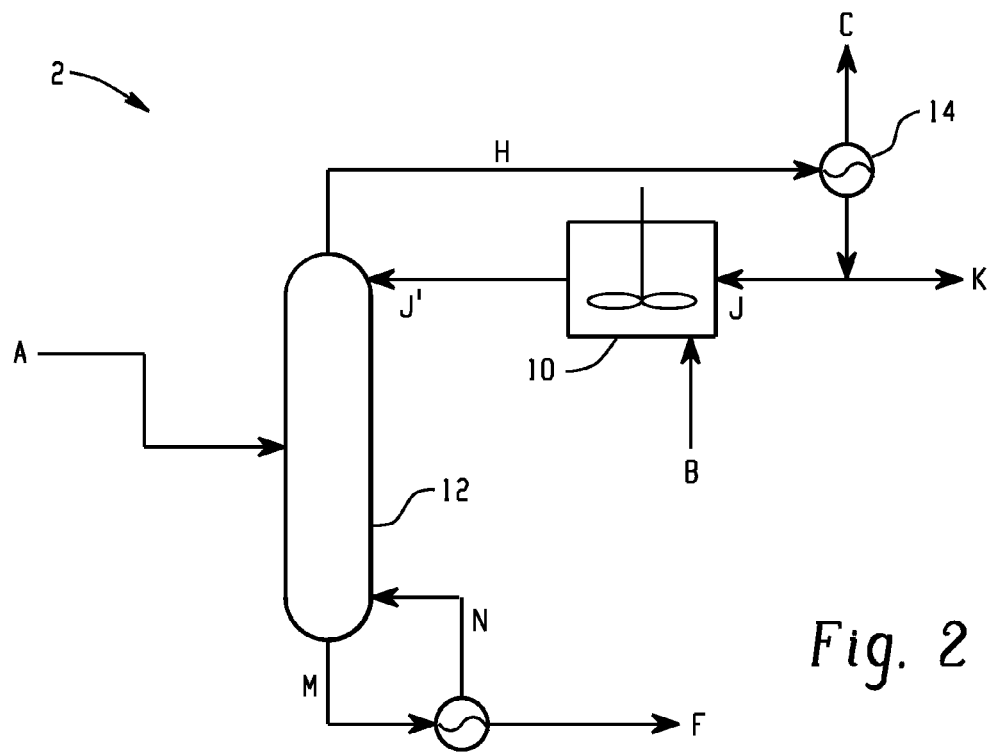
FIG. 2 is a schematic representation of an example of a diaryl carbonate purification scheme by introducing an aqueous media to a diaryl carbonate.

FIG. 2 illustrates a reflux diaryl carbonate purification scheme 2. In purification scheme 2, diphenyl carbonate A that comprises a metal contaminant is introduced to a separation column 12. The reflux stream H that exits at the top of the separation column passes through a condenser 14 where excess of water C is removed. After the condenser 14, the top stream is split into a top stream first portion J and a top stream second portion K, where the top stream second portion K that comprises the purified diaryl carbonate is collected. The top stream first portion J is introduced to a mixing device 10 along with an aqueous stream B, such that any metal contaminant reacts with the water in the aqueous stream and precipitates to form a metal solid form, metal oxides and/or metal hydroxides presumably. After leaving the mixing device 10, the purified stream L is reintroduced to the separation column 12. The bottom stream M that comprises the precipitate exits the bottom of the separation column and is optionally split into a bottom stream first portion N and a bottom stream second portion F. The bottom stream first portion M can be reintroduced into the separation column 12 and the bottom stream second portion F, that comprises diaryl carbonate, non-precipitated, and precipitated metal contaminants is removed from the system.

The purified diaryl carbonate can be used as a reactant along with a dihydroxy compound in the polymerization of a polycarbonate.

A "polycarbonate" means compositions having repeating structural carbonate units of formula (1)

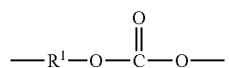

(1)

in which the $R^1$ groups contain aliphatic, alicyclic, and/or aromatic moieties (e.g., greater than or equal to 30 percent, specifically, greater than or equal to 60 percent, of the total number of $R^1$ groups can contain aromatic moieties and the balance thereof are aliphatic, alicyclic, or aromatic). Optionally, each $R^1$ can be a $C_{6-30}$ aromatic group, that is, can contain at least one aromatic moiety. $R^1$ can be derived from a dihydroxy compound of the formula HO—$R^1$—OH, in particular of formula (2)

(2)

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$. Specifically, each $R^1$ can be derived from a dihydroxy aromatic compound of formula (3)

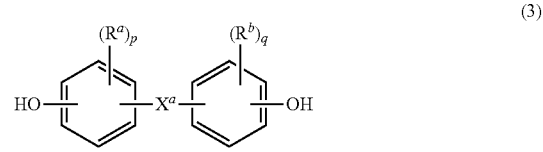

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically, para) to each other on the $C_6$ arylene group. The bridging group $X^a$ can be single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. p and q can each be 1, and $R^a$ and $R^b$ are each a $C_{1-3}$ alkyl group, specifically, methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

$X^a$ can be a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

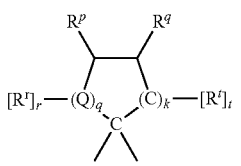

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and i is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group or $R^q$ and $R^t$ taken together can form one aromatic group and $R^r$ and $R^p$ taken together form a second aromatic group. When $R^q$ and $R^t$ taken together form an aromatic group, $R^p$ can be a double-bonded oxygen atom, i.e., a ketone.

Bisphenols (4) can be used in the manufacture of polycarbonates containing phthalimidine carbonate units of formula (4a)

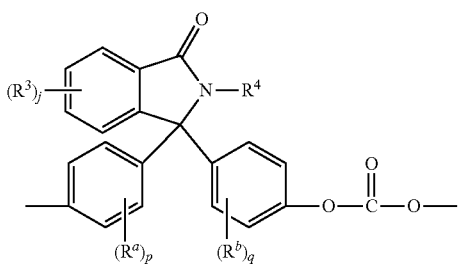

(4a)

wherein $R^a$, $R^b$, p, and q are as in formula (4), $R^3$ is each independently a $C_{1-6}$ alkyl group, j is 0 to 4, and $R_4$ is a $C_{1-6}$ alkyl, phenyl, or phenyl substituted with up to five $C_{1-6}$ alkyl groups. The phthalimidine carbonate units can be of formula (4b)

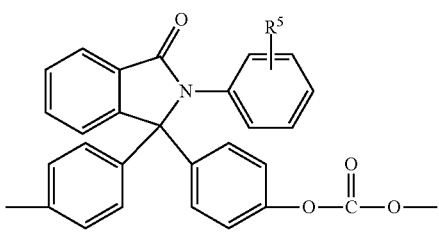

(4b)

wherein $R^5$ is hydrogen or a $C_{1-6}$ alkyl. $R^5$ can be hydrogen. Carbonate units (4a) wherein $R^5$ is hydrogen can be derived from 2-phenyl-3,3'-bis(4-hydroxy phenyl)phthalimidine (also known as N-phenyl phenolphthalein bisphenol, or "PPPBP") (also known as 3,3-bis(4-hydroxyphenyl)-2-phenylisoindolin-1-one).

Other bisphenol carbonate repeating units of this type are the isatin carbonate units of formula (4c) and (4d)

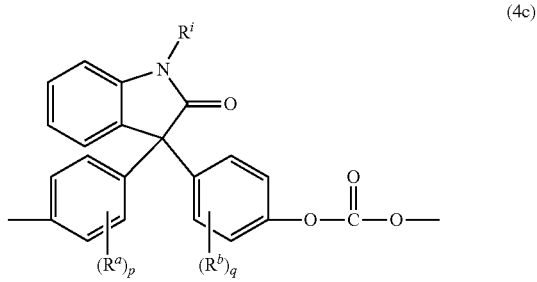

(4c)

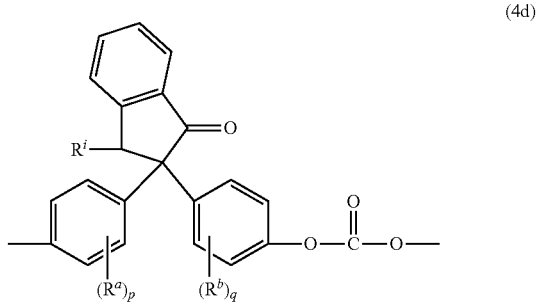

(4d)

wherein $R^a$ and $R^b$ are each independently $C_{1-12}$ alkyl, p and q are each independently 0 to 4, and $R^i$ is $C_{1-12}$ alkyl, phenyl, optionally substituted with 1 5 to $C_{1-10}$ alkyl, or benzyl optionally substituted with 1 to 5 $C_{1-10}$ alkyl. $R^a$ and $R^b$ can each be methyl, p and q can each independently be 0 or 1, and $R^i$ can be $C_{1-4}$ alkyl or phenyl.

Examples of bisphenol carbonate units derived from bisphenols (4) wherein $X^b$ is a substituted or unsubstituted $C_{3-18}$ cycloalkylidene include the cyclohexylidene-bridged, alkyl-substituted bisphenol of formula (4e)

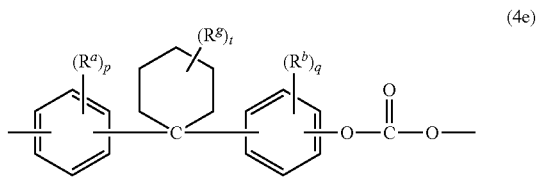

(4e)

wherein $R^a$ and $R^b$ are each independently $C_{1-12}$ alkyl, $R^g$ is $C_{1-12}$ alkyl, p and q are each independently 0 to 4, and t is 0 to 10. At least one of each of $R^a$ and $R^b$ can be disposed meta to the cyclohexylidene bridging group. $R^a$ and $R^b$ can each independently be $C_{1-4}$ alkyl, $R^g$ can be $C_{1-4}$ alkyl, p and q can each be 0 or 1, and t is 0 to 5. $R^a$, $R^b$, and $R^g$ can be each methyl, r and s can be each 0 or 1, and t can be 0 or 3, specifically, 0.

Examples of other bisphenol carbonate units derived from bisphenol (4) wherein $X^b$ is a substituted or unsubstituted $C_{3-18}$ cycloalkylidene include adamantyl units (4f) and units (4g)

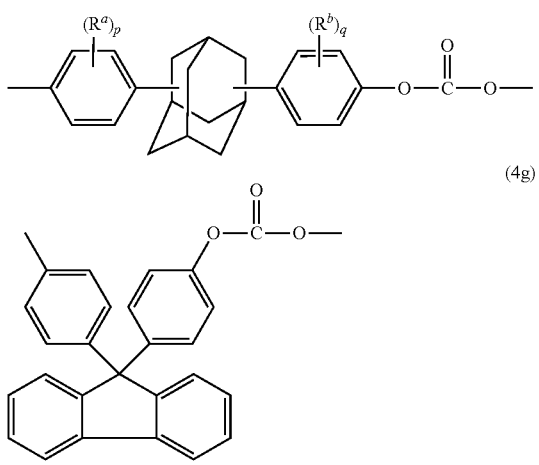

(4f)

(4g)

wherein $R^a$ and $R^b$ are each independently $C_{1-12}$ alkyl, and p and q are each independently 1 to 4. At least one of each of $R^a$ and $R^b$ can be disposed meta to the cycloalkylidene bridging group. $R^a$ and $R^b$ can each independently be $C_{1-3}$ alkyl, and p and q can be each 0 or 1. $R^a$, $R^b$ can be each methyl, p and q can each be 0 or 1. Carbonates containing units (4a) to (4g) are useful for making polycarbonates with high glass transition temperatures (Tg) and high heat distortion temperatures.

Other possible aromatic dihydroxy compounds of the formula HO—$R^1$—OH include compounds of formula (6)

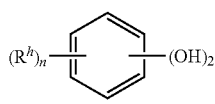

(6)

wherein each $R^b$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen is usually bromine.

Some illustrative examples of specific aromatic dihydroxy compounds (herein also referred to as dihydroxy reactants) include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula (3) include 1,1-bis(4-hydroxyphenyl)methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-2-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl)phthalimidine (PPPBP), and 1,1-bis(4-hydroxy-3-methylphenyl)cyclohexane (DMBPC). Combinations comprising at least one of the foregoing dihydroxy compounds can also be used. The polycarbonate can be a linear homopolymer derived from bisphenol A, in which each of $A^1$ and $A^2$ can be p-phenylene, and $Y^1$ can be isopropylidene in formula (3).

"Polycarbonates" includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates and/or copolycarbonates.

The polycarbonate can be made by a melt polymerization process, which can be a continuous melt process. Generally, in a melt polymerization process, polycarbonates can be prepared by co-reacting, in a molten state, a dihydroxy reactant and a diaryl carbonate (herein also referred to as a diaryl carbonate ester), such as diphenyl carbonate. A useful melt process for making polycarbonates could also use a diaryl carbonate ester having electron-withdrawing substituents on the aryls. Examples of specifically useful diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl)carbonate, bis(2-acetylphenyl)carboxylate, bis(4-acetylphenyl)carboxylate, or a combination comprising at least one of the foregoing esters. The diaryl carbonate ester to dihydroxy reactant can be present in a molar ratio of 2:1 to 1:2, specifically, in a molar ratio of 1.5:1 to 1:1.5, more specifically, in a molar ratio of 1.05:1 to 1:1.05, even more specifically, in a molar ratio of 1:1.

In addition, transesterification catalyst(s) can be employed. Transesterification catalysts used in the melt transesterification polymerization production of polycarbonates can include alpha and/or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkaline earth hydroxides such as magnesium hydroxide and calcium hydroxide. Sources of alkali metal ions can include the alkali metal hydroxides such as illustrated by lithium hydroxide, sodium hydroxide, potassium hydroxide, and combinations comprising at least one of the foregoing. Examples of alkaline earth metal hydroxides are calcium hydroxide, magnesium hydroxide, and combinations comprising at least one of the foregoing. Of these, sodium hydroxide is particularly desirable. The alpha catalyst typically will be used in an amount sufficient to provide $1\times10^{-2}$ to $1\times10^{-8}$ moles, specifically, $1\times10^{-4}$ to $1\times10^{-7}$ moles of metal hydroxide per mole of the dihydroxy compounds employed. Other possible sources of alkaline earth and alkali metal ions include salts of carboxylic acids (such as sodium acetate) and derivatives of ethylene diamine tetraacetic acid (EDTA) (such as EDTA tetrasodium salt, and EDTA magnesium disodium salt), as well as combinations comprising at least one of the foregoing. For example, the alpha catalyst can comprise alkali metal salt(s) of a carboxylic acid, alkaline earth metal salt(s) of a carboxylic acid, or a combination comprising at least one of the foregoing. In another example, the alpha catalyst comprises $Na_2Mg$ EDTA or a salt thereof.

The alpha transesterification catalyst can also, or alternatively, comprise salt(s) of a non-volatile inorganic acid. For example, the alpha catalyst can comprise salt(s) of a non-volatile inorganic acid such as $NaH_2PO_3$, $NaH_2PO_4$, $Na_2HPO_3$, $KH_2PO_4$, $CsH_2PO_4$, $Cs_2HPO_4$, and combinations comprising at least one of the foregoing. Alternatively, or in addition, the alpha transesterification catalyst can comprise mixed alkali metal salt(s) of phosphoric acid, such as $NaKHPO_4$, $CsNaHPO_4$, $CsKHPO_4$, and combinations comprising at least one of the foregoing.

Possible beta catalyst(s) can comprise a quaternary ammonium compound, a quaternary phosphonium compound, or a combination comprising at least one of the foregoing. The quaternary ammonium compound can be organic ammonium compound(s) having structure,

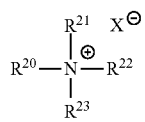

wherein $R^{20}$-$R^{23}$ are independently a $C_1$-$C_{20}$ alkyl radical, $C_4$-$C_{20}$ cycloalkyl radical, or a $C_4$-$C_{20}$ aryl radical; and $X^-$ is an organic or inorganic anion. Optionally, anion $X^-$ can be selected from hydroxide, halide, carboxylate, sulfonate, sulfate, formate, carbonate, and bicarbonate. Some non-limiting examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often employed.

The quaternary phosphonium compound can be of organic phosphonium compounds having structure,

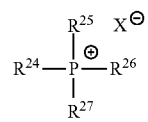

wherein $R^{24}$-$R^{27}$ are independently a $C^1$-$C^{20}$ alkyl radical, $C^4$-$C^{20}$ cycloalkyl radical, or a $C_4$-$C_{20}$ aryl radical; and $X^-$ is an anion (e.g., an organic or inorganic anion). Optionally, anion $X^-$ can be selected from hydroxide, halide, alkoxide, aryloxide, carboxylate, sulfonate, sulfate, formate, carbonate, and bicarbonate. Where $X^-$ is a polyvalent anion such as carbonate or sulfate it is understood that the positive and negative charges in the quaternary ammonium and phosphonium structures are properly balanced. For example, where $R^{20}$-$R^{23}$ are each methyl groups and $X^-$ is carbonate, it is understood that $X^-$ represents $2(CO_3^{-2})$.

Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often employed.

The amount of beta catalyst employed is typically based upon the total number of moles of dihydroxy compound employed in the polymerization reaction. When referring to the ratio of beta catalyst, for example, phosphonium salt, to all dihydroxy compounds employed in the polymerization reaction, it is convenient to refer to moles of phosphonium salt per mole of the dihydroxy compound(s), meaning the number of moles of phosphonium salt divided by the sum of the moles of each individual dihydroxy compound present in the reaction mixture. The amount of beta catalyst (e.g., organic ammonium or phosphonium salts) employed typically will be $1\times10^{-2}$ to $1\times10^{-5}$, specifically, $1\times10^{-3}$ to $1\times10^{-4}$ moles per total mole of the dihydroxy compounds in the reaction mixture.

Polycarbonates polymerized from such a purified diaryl carbonate can have a low color value of, for example a CIE b* index of less than or equal to 0.5, specifically, less than or equal to 0.15 as determined by spectrophotometry and high light transmission of, for example, greater than or equal to 89% as determined by spectrophotometry.

The following examples are provided to illustrate the purification process. The examples are merely illustrative and are not intended to limit devices made in accordance with the disclosure to the materials, conditions, or process parameters set forth therein.

EXAMPLES

Example 1

Figure 3:
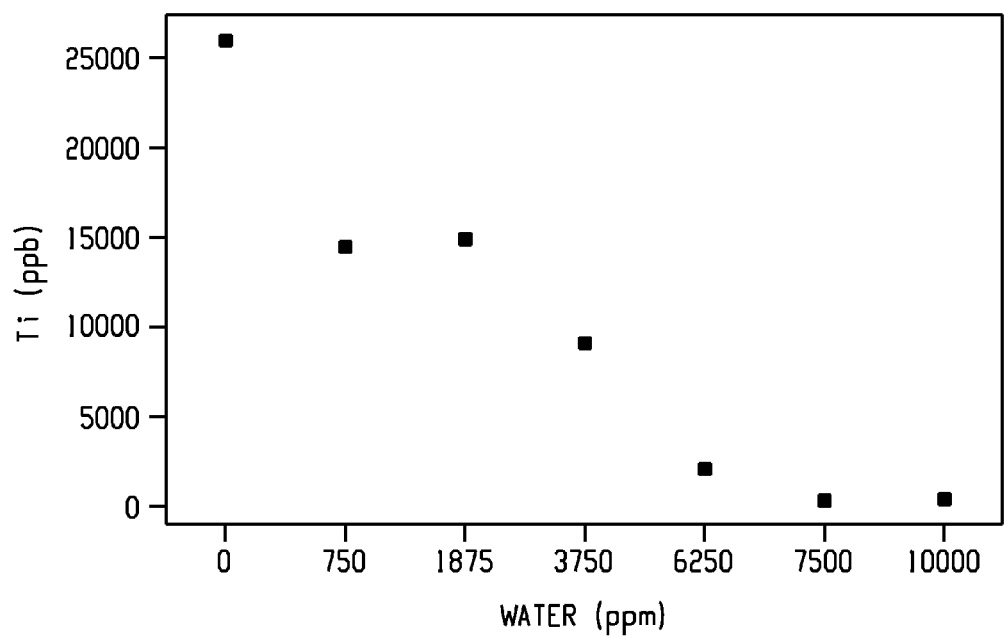
FIG. 3 is a graphical illustration of the titanium levels versus water concentration of Example 1 with a contact time of 3.6 minutes (min)
Figure 4:
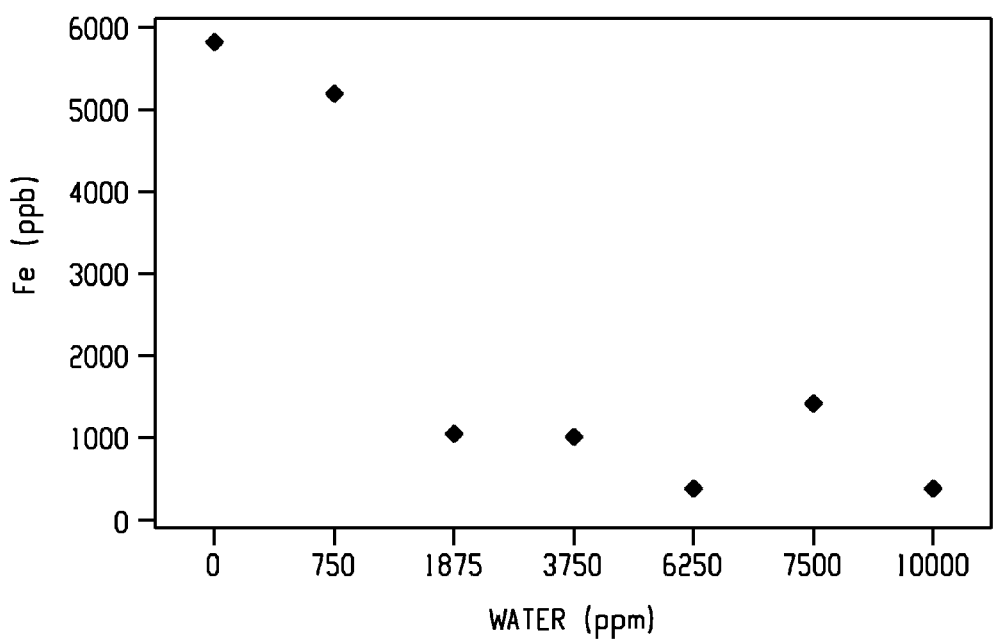
FIG. 4 is a graphical illustration of the iron levels versus water concentration of Example 1 with a contact time of 3.6 min.

A diphenyl carbonate (DPC) stream of containing 25861 parts per billion by weight (ppb) of Ti and 5826 ppb of Fe, measured by inductively coupled plasma optical emission spectrometry (ICP-OES)), in soluble organometallic form was mixed with a set of different flow rates of water in a pressurized continuously stirred tank reactor (CSTR) at 15 bar-gauge (barg) and 170 degrees Celsius (° C.) (residence time=3.6 minutes (min). After exiting the CSTR, the stream was filtered using a filter with a mesh size of 0.20 micrometers to remove the precipitated metal contaminant. FIGS. 3 and 4 show Ti and Fe levels, respectively, of the treated sample after filtration, where the x-axis represents ppm of water, i.e. milligrams per hour (mg/h) of water divided by kilograms per hour (kg/h) of DPC, while the y-axis represents ppb of organic soluble metal. These results show that with just 6250 ppm of water, the removal of metals, for both Ti and Fe, is greater than the 90 wt %.

Example 2

A DPC stream containing 99.51 wt % DPC, 0.27 wt % bisphenol A (BPA), 0.19% of high boiling point impurities (HBs), also containing 25861 ppb of Ti and 5826 ppb of Fe in soluble organometallic form (similar to Example 1), was fed to the 14$^{th}$ stage of a distillation column with 19 theoretical stages in order to obtain a purified DPC product. The vacuum pressure at the top of this column was 12 millibar (mbar).

The residue bottom stream from this column contained the higher boiling point impurities, while the distillate top stream contained 15631 kg/h of 99.99 wt % DPC and 0.01 wt % of PMC, with 30 ppb of residual Ti and 60 ppb of residual iron.

Example 3

A feed stream similar to Example 2 (99.51 wt % DPC, 0.27 wt % BPA, 0.19 wt % HBs, also containing 25861 ppb of Ti and 5826 ppb of Fe in soluble organometallic form) was mixed with 99 kg/h of water in a specially designed static mixer working at 170° C. As was done in Example 2, effluent from the static mixer was sent to a distillation column, where a further DPC purification step was performed. High boiling impurities as well as the solid products generated in the hydrolysis process were recovered from the bottom stream of this column. The DPC product from this column was obtained as distillate from the column with less than 1 ppb of Ti and Fe residuals, and less than 250 ppm of water. Additionally, 72.6 kg/h of phenol was recovered as distillate which was generated from the hydrolysis of diphenyl carbonate with water in the static mixer. Excess water was vented as vapor to the vacuum system.

Example 4

Figure 5:
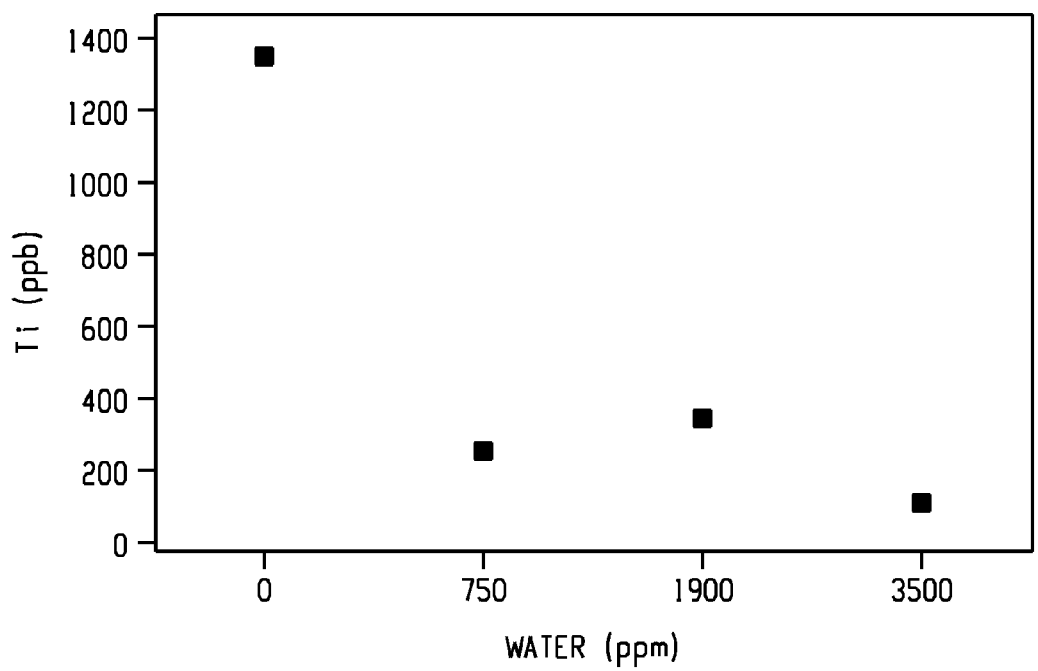
FIG. 5 is a graphical illustration of the titanium levels versus water concentration of Example 4 with a contact time of 7.6 min.
Figure 6:
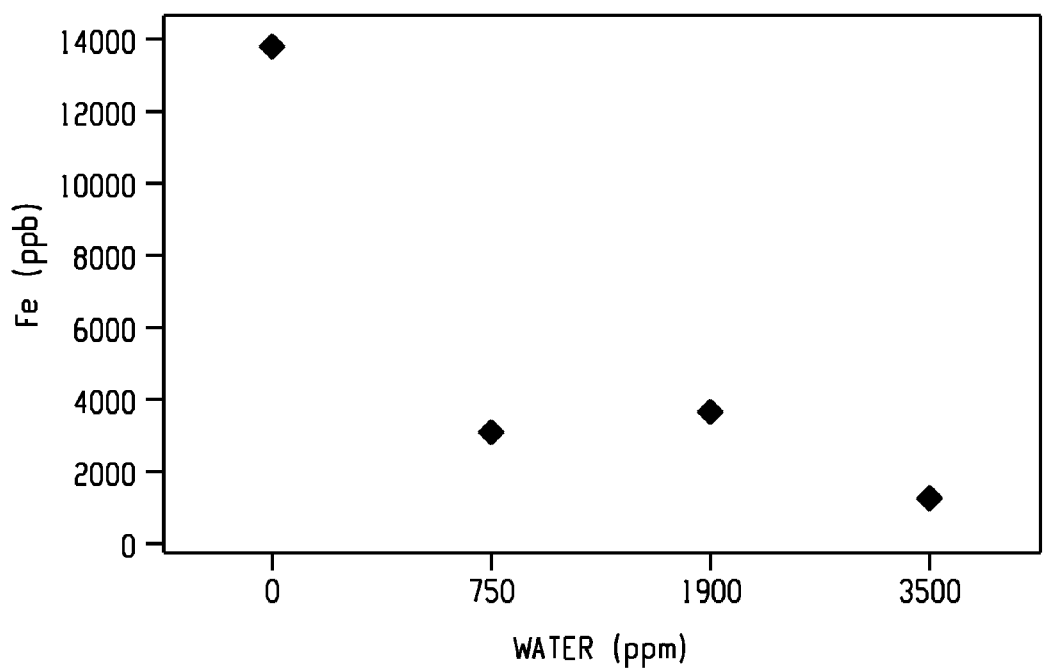
FIG. 6 is a graphical illustration of the iron levels versus water concentration of Example 4 with a contact time of 7.6 min.

A stream of DPC containing 1364 ppb of Ti and 13897 ppb of Fe in soluble organometallic form was mixed with a set of different flows of water in a pressurized CSTR at 15 barg and 170° C. (contact time=7.6 min). After exiting the CSTR, the stream was filtered using a filter with a mesh size of 0.20 micrometers to remove the precipitated metal contaminants. FIGS. 5 and 6 show Ti and Fe levels, respectively, of the treated sample of the sample after filtration, where the x-axis represents ppm of water, i.e. mg/h of water divided by kg/h of DPC, while the y-axis represents ppb of organic soluble metal. These results show that with just 3500 ppm of $H_2O$, the removal of metals, for both Ti and Fe, is greater than the 90 wt %.

The effluent stream of either of Examples 1 or 2 with a reduced level of contaminant metal can be further purified using a separation column or a set of cascading separation columns to obtain even higher purity DPC.

Set forth below are some embodiments of the method for making the purified diaryl carbonate disclosed herein and the diaryl carbonate made thereby.

Embodiment 1 a process for purifying a diaryl carbonate, comprising: introducing an aqueous stream to a diaryl carbonate stream that comprises a metal contaminant, wherein the aqueous stream reacts with the metal contaminant to form a precipitate; wherein introducing the aqueous stream to the contaminated diaryl carbonate stream results in introducing 100 to 10,000 ppm water based on the total composition of the diaryl carbonate stream and the aqueous stream; removing the precipitate via one or both of a separation column and a filter to result in a purified diaryl carbonate. When the removing utilizes the separation column, the process further comprises: removing a bottom stream comprising the precipitate from the separation column; directing a bottom stream first portion into the separation column and collecting a bottom stream second portion; removing a top stream from the separation column; directing a top stream first portion into the separation column and collecting a top stream second portion, wherein the top stream second component comprises the purified diaryl carbonate.

Embodiment 2 a process for purifying a diaryl carbonate, comprising: introducing an aqueous stream to a diaryl carbonate stream that comprises molten diaryl carbonate and a metal contaminant, wherein the aqueous stream reacts with the metal contaminant to form a precipitate; wherein introducing the aqueous stream to the diaryl carbonate stream results in introducing 100 to 10,000 ppm water based on the total composition of the diaryl carbonate stream and the aqueous stream; and removing the precipitate via one or both of a separation column and a filter to result in a purified diaryl carbonate. Optionally, when the removing utilizes the separation column, the process can further comprise: removing a bottom stream comprising the precipitate from the separation column; removing a top stream from the separation column; and directing a top stream first portion into the separation column and collecting a top stream second portion, wherein the top stream second component comprises the purified diaryl carbonate.

Embodiment 3 the process of any of Embodiments 1-2, wherein the removing utilizes the separation column, and wherein the introducing occurs before the diaryl carbonate stream enters the separation column.

Embodiment 4 the process of any of Embodiments 1-3, wherein the removing utilizes the separation column, and wherein the introducing occurs before the top stream first portion is directed into the separation column.

Embodiment 5 the process of any of Embodiments 1-4, wherein the removing utilizes the filter.

Embodiment 6 the process of any of Embodiments 1-5, wherein the metal contaminant comprises titanium, lead, tin, zirconium, molybdenum, niobium, vanadium, iron, zinc, aluminum, yttrium, lanthanum, hafnium, tungsten, neodymium, samarium, ytterbium, copper, chromium, nickel, manganese, bismuth, niobium, or a combination comprising one or more of the foregoing.

Embodiment 7 the process of any of Embodiments 1-6, wherein the metal contaminant comprises titanium, iron, or a combination comprising one or both of the foregoing.

Embodiment 8 the process of any of Embodiments 1-7, wherein greater than or equal to 90 wt % of the metal contaminant is removed based on the total weight of the metal contaminant present in the diaryl carbonate stream.

Embodiment 9 the process of any of Embodiments 1-8, further comprising preparing the diaryl carbonate.

Embodiment 10 the process of Embodiment 9, wherein the preparing comprises the step of decarbonylating a diaryl oxalate in the presence of a decarbonylation catalyst.

Embodiment 11 the process of Embodiment 10, wherein the diaryl oxalate has the formula: ArO(C=O)—(C=O)OAr, where each Ar independently is an aromatic hydrocarbon group having 6 to 14 carbon atoms.

Embodiment 12 the process of any of Embodiments 10-11, wherein the catalyst comprises an organic phosphorus compound.

Embodiment 13 the process of Embodiment 9, wherein the preparing comprises the reacting an aromatic hydroxy compound and carbon monoxide in the presence of oxygen and a catalyst.

Embodiment 14 the process of Embodiment 13, wherein the catalyst comprises a palladium catalyst.

Embodiment 15 the process of Embodiment 9, wherein the preparing comprises reacting an aromatic hydroxy compound with either phosgene or a dialkyl carbonate in the presence of a transesterification catalyst.

Embodiment 16 the process of any of Embodiments 13-15, wherein the aromatic hydroxy compound has the formula (III)

$$(R_2)_n \text{—Ar—OH} \quad (III)$$

wherein n is an integer 1 to 3 and each $R_2$ is independently linear or branched, optionally substituted $C_{1-34}$ alkyl, specifically, $C_{1-6}$ alkyl, more specifically, $C_{1-4}$ alkyl; $C_{1-34}$ alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; optionally branched $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl.

Embodiment 17 the process of any of Embodiments 1-16, wherein the diaryl carbonate has the formula (I)

$$(R_2)_n\text{—Ar—O—C(=O)—O—Ar—}(R_2)_n \quad (I)$$

wherein n is an integer 1 to 3 and each $R_2$ is independently linear or branched, optionally substituted $C_{1-34}$ alkyl, specifically, $C_{1-6}$ alkyl, more specifically, $C_{1-4}$ alkyl; $C_{1-34}$ alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; optionally branched $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl.

Embodiment 18 the process of any of Embodiments 1-17, wherein the diaryl carbonate stream comprises greater than or equal to 50 wt % diaryl carbonate based on the total weight of the diaryl carbonate stream.

Embodiment 19 the process of any of Embodiments 1-18, wherein the diaryl carbonate stream comprises greater than or equal to 70 wt % diaryl carbonate based on the total weight of the diaryl carbonate stream.

Embodiment 20 the process of any of Embodiments 1-19, the diaryl carbonate stream comprises greater than or equal to 90 wt % diaryl carbonate based on the total weight of the diaryl carbonate stream.

Embodiment 21 the process of any of Embodiments 1-20, wherein the diaryl carbonate stream comprises greater than or equal to 95 wt % diaryl carbonate based on the total weight of the diaryl carbonate stream.

Embodiment 22 the process of any of Embodiments 1-21, wherein the diaryl carbonate stream comprises greater than or equal to 99 wt % diaryl carbonate based on the total weight of the diaryl carbonate stream.

Embodiment 23 the process of any of Embodiments 1-22, wherein the diaryl carbonate stream comprises molten diaryl carbonate, or wherein the diaryl carbonate stream is molten diaryl carbonate and the metal contaminant.

Embodiment 24 the process of any of Embodiments 1-23, wherein the diaryl carbonate stream consists of the diaryl carbonate and the metal contaminant.

Embodiment 25 the process of any of Embodiments 1-24, wherein the introducing occurs at a temperature of greater than 80° C.

Embodiment 26 the process of any of Embodiments 1-25, wherein the introducing occurs at a temperature of greater than 100° C.

Embodiment 27 the process of any of Embodiments 1-26, wherein the introducing occurs at a temperature of 110° C. to 250° C.

Embodiment 28 the process of any of Embodiments 1-27, wherein the introducing occurs at a temperature of greater than or equal to 120° C. to 250° C.

Embodiment 29 the process of any of Embodiments 1-28, wherein the separation column comprises a cascade of separation columns.

Embodiment 30 the process of any of Embodiments 1-29, wherein the filter is located upstream of and/or downstream of the separation column.

Embodiment 31 the process of any of Embodiments 1-30, wherein the separation column is located upstream of and/or downstream of the filter

Embodiment 32 the process of any of Embodiments 1-2 and 5-28, wherein the removing utilizes only the filter.

Embodiment 33 the process of any of Embodiments 1-4 and 6-29, wherein the removing utilizes only the separation column.

Embodiment 34 the process of any of Embodiments 1-33, wherein the introducing occurs in the presence of 0 to 50 wt % of a solvent based on the total weight of the diaryl carbonate stream and the aqueous stream.

Embodiment 35 the process of any of Embodiments 1-34, wherein the introducing occurs in the presence of 0 to 25 wt % of a solvent based on the total weight of the diaryl carbonate stream and the aqueous stream.

Embodiment 36 the process of any of Embodiments 1-35, wherein the introducing occurs in the presence of 0 to 1 wt % of a solvent based on the total weight of the diaryl carbonate stream and the aqueous stream.

Embodiment 37 the process of any of Embodiments 1-36, wherein the introducing occurs in the presence of 0 wt % of a solvent based on the total weight of the diaryl carbonate stream and the aqueous stream.

Embodiment 38 the process of Embodiment 1, wherein the introducing occurs in a mixing device.

Embodiment 39 a purified diaryl carbonate made from any of Embodiments 1-38.

Embodiment 40 a polycarbonate made from the purified diaryl carbonate of Embodiment 39 and a dihydroxy compound.

Embodiment 41 the polycarbonate of Embodiment 40, wherein the polycarbonate has one or both of a CIE b* index of less than or equal to 0.5 as determined by spectrophotometry and a light transmission of greater than or equal to 89% as determined by spectrophotometry.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements can be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A process for purifying a diaryl carbonate, comprising:
reacting an aromatic hydroxy compound with a dialkyl carbonate in the presence of a transesterification catalyst to form the diaryl carbonate;
introducing an aqueous stream to a molten stream that comprises the diaryl carbonate and a metal contaminant, wherein the molten stream comprises greater than or equal to 90 wt % of the diaryl carbonate based on the total weight of the molten stream, wherein the introducing occurs at a temperature of 120° C. to 250° C., wherein the aqueous stream reacts with the metal contaminant to form a precipitate; wherein introducing the aqueous stream to the molten stream results in introducing 100 to 8,000 ppm water based on the total composition of the molten stream;
removing the precipitate via one or both of a separation column and a filter to result in a purified diaryl carbonate;
wherein when the removing utilizes the separation column, the process further comprises:
removing a bottom stream comprising the precipitate from the separation column;
removing a top stream from the separation column;
directing a top stream first portion into the separation column and collecting a top stream second portion, wherein the top stream second portion comprises the purified diaryl carbonate.

2. The process of claim 1, wherein the removing utilizes the separation column, and wherein the introducing occurs before the molten stream enters the separation column.

3. The process of claim 1, wherein the removing utilizes the separation column, and wherein the introducing occurs before the top stream first portion is directed into the separation column.

4. The process of claim 1, wherein the removing utilizes the filter.

5. The process of claim 1, wherein the metal contaminant comprises titanium, lead, tin, zirconium, molybdenum, niobium, vanadium, iron, zinc, aluminum, yttrium, lanthanum, hafnium, tungsten, neodymium, samarium, ytterbium, copper, chromium, nickel, manganese, bismuth, or a combination comprising one or more of the foregoing.

6. The process of claim 1, wherein greater than or equal to 90 wt % of the metal contaminant is removed based on the total weight of the metal contaminant present in the molten stream.

7. The process of claim 1, wherein the aromatic hydroxy compound has the formula (III)

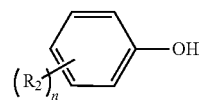

wherein n is an integer from 1 to 3 and each $R_2$ is independently a $C_{1-34}$ alkyl, a $C_{1-34}$ alkoxy, a $C_{5-34}$ cycloalkyl, a $C_{7-34}$ alkylaryl, a $C_{6-34}$ aryl, a halogen radical, or —COO—R', wherein R' is H, a $C_{1-34}$ alkyl, $C_{1-34}$ alkoxy, $C_{5-34}$ cycloalkyl, $C_{7-34}$ alkylaryl, or $C_{6-34}$ aryl.

8. The process of claim 1, wherein the diaryl carbonate has the formula (I)

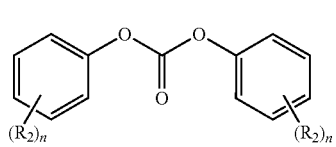

wherein n is an integer from 1 to 3 and each $R_2$ is independently, a $C_{1-34}$ alkyl, a $C_{1-34}$ alkoxy, a $C_{5-34}$ cycloalkyl, a $C_{7-34}$ alkylaryl; a $C_{6-34}$ aryl; a halogen radical, or —COO—R', wherein R' is H, a $C_{1-34}$ alkyl, a $C_{1-34}$ alkoxy, a $C_{5-34}$ cycloalkyl, a $C_{7-34}$ alkylaryl; or a $C_{6-34}$ aryl.

9. The process of claim 1, wherein the introducing occurs in a mixing device.

10. The process of claim 1, wherein the aromatic hydroxy compound is phenol and the diaryl carbonate is diphenyl carbonate; wherein the molten stream comprises greater than or equal to 99 wt % diphenyl carbonate based on the total weight of the molten stream.

11. The process of claim 1, wherein the purified diaryl carbonate comprises less than or equal to 38 ppb of molybdenum; less than or equal to 38 ppb of vanadium; less than or equal to 38 ppb of chromium; less than or equal to 85 ppb of titanium; less than or equal to 425 ppb of niobium; less than or equal to 38 ppb of nickel; less than or equal to 12 ppb of zirconium; less than or equal to 12 ppb of iron, or a combination comprising one or more of the foregoing based on a total weight of the purified diaryl carbonate.

12. The process of claim 10, wherein the purified diaryl carbonate comprises less than or equal to 38 ppb of molybdenum; less than or equal to 38 ppb of vanadium; less than or equal to 38 ppb of chromium; less than or equal to 85 ppb of titanium; less than or equal to 425 ppb of niobium; less than or equal to 38 ppb of nickel; less than or equal to 12 ppb of zirconium; less than or equal to 12 ppb of iron, or a combination comprising one or more of the foregoing based on a total weight of the purified diaryl carbonate.

13. The process of claim 10, wherein the metal contaminant comprises iron and titanium.

* * * * *